US 8,231,864 B2

(12) United States Patent
Grandmaire et al.

(10) Patent No.: US 8,231,864 B2
(45) Date of Patent: Jul. 31, 2012

(54) OLIGOMERIC AMIDOAMINES OR AMIDOQUATS FOR FABRIC OR HAIR TREATMENT COMPOSITIONS

(75) Inventors: Jean-Paul Grandmaire, Andrimont (BE); Leopold Laitem, Lebanon, NJ (US); Amjad Farooq, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 831 days.

(21) Appl. No.: 11/994,345

(22) PCT Filed: Jun. 29, 2006

(86) PCT No.: PCT/US2006/025735
§ 371 (c)(1),
(2), (4) Date: Aug. 4, 2008

(87) PCT Pub. No.: WO2007/002913
PCT Pub. Date: Jan. 4, 2007

(65) Prior Publication Data
US 2009/0202466 A1    Aug. 13, 2009

Related U.S. Application Data

(60) Provisional application No. 60/694,966, filed on Jun. 29, 2005.

(51) Int. Cl.
*A61K 8/42* (2006.01)
*A61Q 5/12* (2006.01)
*C11D 3/32* (2006.01)
*C07C 237/10* (2006.01)
(52) U.S. Cl. ........................ 424/70.17; 510/515; 564/153
(58) Field of Classification Search ............... 424/70.17; 510/515; 564/153
See application file for complete search history.

(56) References Cited

U.S. PATENT DOCUMENTS

| | | | | |
|---|---|---|---|---|
| 3,224,893 A | * | 12/1965 | Floyd et al. | .................. 106/316 |
| 3,915,867 A | | 10/1975 | Kang et al. | |
| 4,732,966 A | | 3/1988 | Wilson | |
| 4,830,771 A | | 5/1989 | Ruback et al. | |
| 4,954,335 A | | 9/1990 | Janchipraponvej | |
| 5,200,097 A | | 4/1993 | Hughes et al. | |
| 5,501,806 A | | 3/1996 | Farooq et al. | |
| 5,939,377 A | | 8/1999 | Ewbank et al. | |
| 6,020,304 A | | 2/2000 | Ceulemans et al. | |
| 6,525,016 B2 | | 2/2003 | Liew | |
| 6,653,436 B2 | | 11/2003 | Back et al. | |
| 6,881,716 B2 | | 4/2005 | Grandmaire et al. | |
| 2004/0048754 A1 | | 3/2004 | Herrmann et al. | |
| 2004/0131576 A1 | | 7/2004 | Decoster et al. | |

FOREIGN PATENT DOCUMENTS

| | | | |
|---|---|---|---|
| EP | 0038862 | | 11/1981 |
| EP | 0459211 A2 | | 12/1991 |
| EP | 1136471 | | 9/2001 |
| GB | 1 494 916 | * | 12/1977 |
| GB | 2170813 A | | 8/1986 |
| JP | 2002-173889 | * | 6/2002 |
| SU | 351865 | | 9/1972 |

OTHER PUBLICATIONS

International Search Report, Nov. 21, 2006.
Chinese Office Action Dated Feb. 12, 2010.

* cited by examiner

*Primary Examiner* — Robert A Wax
*Assistant Examiner* — Aradhana Sasan
(74) *Attorney, Agent, or Firm* — Michael F. Morgan

(57) ABSTRACT

Provided are oligomeric amidoamines, an oligomeric amidoamine salt of the oligomeric amidoamine, and/or an oligomeric amidoquat of the oligomeric amidoamine. These materials can be used as fabric softeners in fabric softener compositions or as a hair treatment in hair treatment compositions.

15 Claims, No Drawings

OLIGOMERIC AMIDOAMINES OR AMIDOQUATS FOR FABRIC OR HAIR TREATMENT COMPOSITIONS

CROSS REFERENCE TO RELATED APPLICATIONS

This application is a national stage entry under 35 U.S.C. §371 of International Patent Application No. PCT/US2006/025735, filed 29 Jun. 2006, which claims priority to U.S. Provisional Patent Application No. 60/694,966, filed on 29 Jun. 2005, which are incorporated herein by reference.

BACKGROUND OF THE INVENTION

Biodegradable softeners are described in the prior art. Compositions containing quaternary ammonium salts having at least one long chain hydrocarbyl group are commonly used to provide fabric softening benefits when used in a laundry rinse operation.

Oligomeric esteramines and oligomeric esterquats are compounds commonly described in the prior art to effect fabric softening. These compounds are sensitive to hydrolysis and can degrade over time. Consequently, softening compositions in which these ingredients are present lose some of their ability to soften fabric over time. Correspondingly, clear softening compositions obtained with oligomeric esterquats become turbid or cloudy due to the increased content of fatty acid generated by hydrolysis.

Accordingly, there is a need in the art for improving the stability of oligomeric-type amines and quats while retaining their softening efficacy and ability to provide clear or transparent or translucent compositions.

SUMMARY OF THE INVENTION

In one aspect of the invention, provided is an oligomeric amidoamine comprising a reaction product of (A), (B), and (C) wherein:
(A) represents an alkylene polyamine having the formula:

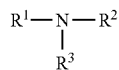

wherein $R^1$, $R^2$, $R^3$ are independently H or $-R^5-N-(R^4)_2$, wherein not all of $R^1$, $R^2$, and $R^3$ are H;
$R^4$ is H or $-R^5-N-(R^8)_2$;
$R^8$ is independently H or $R^5$; and $R^5$ is (i) a $C_1$-$C_{23}$ alkylene or alkenyl group optionally substituted or branched; or (ii) an aryl group;
(B) represents a dicarboxylic acid or a reactive derivative of such acid having the formula:

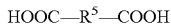

wherein $R_5$ is defined as above; and
(C) represents
(i) a fatty acid having the formula:

wherein $R^6$ is a linear or branched $C_6$-$C_{23}$ alkyl or alkenyl group; and/or
(ii) an alkyl ester or glyceride of the fatty acid (i).

DETAILED DESCRIPTION OF THE INVENTION

As used throughout, ranges are used as a shorthand for describing each and every value that is within the range. Any value within the range can be selected as the terminus of the range.

In one embodiment, the invention relates to oligomeric amidoamines, amidoamine salts, and oligomeric amidoquaternary ammonium compounds (amidoquats). More particularly, the invention relates to such oligomeric amidoamines, oligomeric amidoamine salts, and amidoquats which are obtained by the amidation reaction of an alkylene polyamine with a fatty acid in the presence of a dicarboxylic acid or diester. The oligomeric amidoamine may then be esterified with fatty alcohol or quaternized to form the amidoamine salt or the amidoquat, respectively.

In one embodiment, oligomeric refers to structures having 2 to 10 repeating units. In another embodiment, oligomeric refers to structures having 2 to 5, 2 to 4, or 2 to 3 repeating units.

The softening compositions of the invention comprising an oligomeric amidoamine compound are generally aqueous compositions which may be milky, opaque, clear, transparent or translucent. The compositions may also be liquid or solid.

In one embodiment, the invention provides hair treatment compositions comprising an oligomeric amidoamine compound, an oligomeric amidoamine salt, and/or an amidoquat compound that may be used in a conventional manner to condition hair.

In one embodiment, the invention provides fabric softening compositions comprising an oligomeric amidoamine compound, an oligomeric amidoamine salt, and/or an amidoquat compound that may be used in a conventional manner in the rinse cycle of a washing machine in the form of an aqueous dispersion, but also in the form of a liquid, powder, or solid product that can be used during the washing or drying steps of the fabric treatment process.

In a dryer, for example, the product may be in the form of a substrate, such as a sheet or sponge-type material, impregnated with the oligomeric amidoamine derivative.

The amidation reaction to provide the oligomeric amidoamine or amidoamine salt or amidoquat of the invention is obtained by the reaction of an alkylene polyamine as defined herein with a dicarboxylic acid or a reactive derivative as set forth above.

The polyalkylene polyamine includes, but is not limited to, diethylene triamine, dipropylene triamine, hexamethylene diamine, bis(hexamethylene)triamine, triethylene tetraamine, and tris(2-aminoethyl)amine.

The dicarboxylic acid includes, but is not limited to, succinic acid, malic acid, glutaric acid, adipic acid, and maleic acid. The short esters, anhydrides or chloride derivatives of these acids may be used as methyl of ethyl esters. In one embodiment, the dicarboxylic acid is adipic acid.

The fatty acid reactant may be derived from vegetable and/or animal oils and/or fats, such as, coconut, tallow, and palm, and may be partially or fully hydrogenated. The fatty acids may optionally be synthetic acids such as, lauric, palmetic, and oleic.

The molar ratio of dicarboxylic acid (B) to alkylene polyamine (A) is generally about 0.2 to about 1.2, preferably about 0.5 to about 0.8.

The molar ratio of fatty acid (C) to polyamine (A) is about 0.2 to about 2.0, preferably about 0.5 to about 1.5.

A fatty alcohol or polyalkoxylated fatty alcohol of the general formula $R^6-O-(CR^7HCH_2O)_n-H$ where n=0 to 10 and $R^6$ is as defined above, and $R^7$ is H or $R^5$.

The oligomeric amidoamine may be used as an amine salt by neutralizing the amine with mineral or organic acids such as hydrochloric, sulfuric, phosphoric, citric or lactic acids. Alternatively, it may be used as a quaternary ammonium compound when quaternized with conventional alkylation agents such as methyl chloride or dimethyl sulfate. The oligomeric amidoamine or derivative may be obtained by controlled alkoxylation of the oligomeric amidoamine.

Clear or translucent compositions may be obtained by selecting a molar ratio as herein described and/or using unsaturated fatty acids or alcohols.

The oligomeric amidoamine is used as the main active ingredient in fabric softening compositions or hair conditioners that may also contain nonionic fabric conditioning surfactants, cationic softeners, co-softening ingredients such as silicones, anionic surfactants, and amphoteric surfactants; stabilizers such as non-ionic surfactants (ethoxylated fatty alcohols, amines or acids); inorganic salts or thickening agents to stabilize the fabric softening composition viscosity; pH adjusting compounds such as inorganic or organic acids or bases; and added benefit ingredients such as soil release polymers and antibacterial compounds.

Preferably cationic softeners are also present, and especially preferred are softeners such as esterquats, imidazolinium quats, difatty diamido ammonium methyl sulfate, and ditallow dimethyl ammonium chloride. Suitable cationic softeners are described in U.S. Pat. No. 5,939,377; U.S. Pat. No. 6,020,304; U.S. Pat. No. 4,830,771; and U.S. Pat. No. 5,501,806; the disclosures of which are incorporated herein by reference.

A preferred cationic softener for the invention is produced by reacting two moles of fatty acid methyl ester with one mole of triethanolamine followed by quaternization with dimethyl sulfate (further details on this preparation method are disclosed in U.S. Pat. No. 3,915,867, which is incorporated herein by reference). The reaction products are 50% diesterquat, 20% monoester form, and 30% triester form. In the present specification, the above reaction product mixture of triethanol amine esterquat is often referred to simply as esterquat. It is commercially available from Kao Corp. as Tetranyl AT1-75™.

Another preferred softener comprises a fatty ester quaternary ammonium compound represented by the formula:

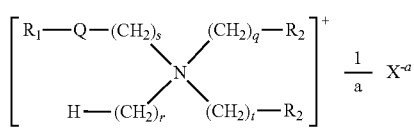

wherein Q represents a carboxyl group having the structure —OCO— and/or —COO—; $R_1$ represents an aliphatic hydrocarbon group having 8 to 22 carbon atoms; $R_2$ represents -Q-$R_1$ and/or —OH; q, r, s and t, each independently represent a number of 1 to 3; and $X^{-a}$ is an anion of valence a; and wherein the fatty ester quaternary ammonium compound is comprised of a distribution of monoester, diester and triester compounds, the monoester compound being formed when each $R_2$ is —H; the diester compound being formed when one $R_2$ is —OH and the other $R_2$ is -Q-$R_1$; and the triester compound being formed when each $R_2$ is -Q-$R_1$; and wherein the normalized percentage of monoester compound in the fatty ester quaternary ammonium compound is about 31% to about 37%; the normalized percentage of diester compound is about 53% to about 59% and the normalized percentage of triester compound is about 8% to about 12%; all percentages being by weight.

EXAMPLES

The following prophetic examples are illustrative only and do not limit the invention.

In Examples 1-4 in the table below, the materials can be reacted together at a combination of temperature and pressure for amidation of the amine.

| Example | Amine (A) | Dicarboxylic Acid (B) | Fatty Acid (C) | Fatty Alcohol |
|---|---|---|---|---|
| 1 | Diethylene triamine 3 moles | Adipic acid 1.5 moles | H-tallow 1.5 moles | |
| 2 | Diethylene triamine 3 moles | Adipic acid 1.5 moles | H-tallow 1.5 moles | H-tallow 0.2 moles |
| 3 | Tris(2-amino ethyl) amine 4 moles | Adipic acid 3 moles | H-tallow 1.5 moles | |
| 4 | Tris(2-amino ethyl) amine 4 moles | Adipic acid 3 moles | H-tallow 1.5 moles | H-tallow 0.2 moles |

The resulting oligomeric amidoamines may be dissolved in low molecular weight alcohol (ethanol and/or isopropanol) to make handling easier.

The oligomeric amidoamines may be quaternized by mixing with 8% by weight isopropyl alcohol and a stoichiometric amount of dimethyl sulfate or methyl chloride to quaternize the amine sites.

An oligomeric amidoamine of Example 1 can have the following structure:

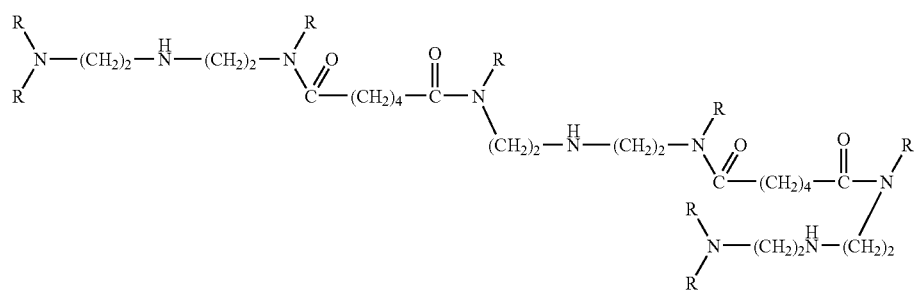

wherein R is H, a 1-22 carbon atom alkyl group, a 1-22 carbon atom alkenyl group, and/or

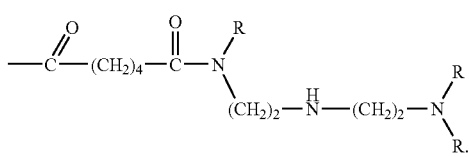

As alternatives to Examples 2 and 4, 0.6 moles of H-Tallow alcohol can be used.

An oligomeric amidoamine of Example 3 can have the following structure:

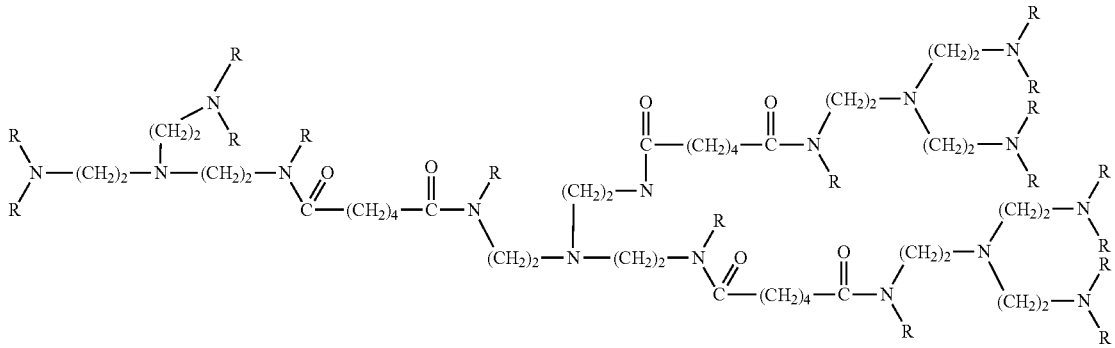

wherein R is H, a 1-22 carbon atom alkyl group, a 1-22 carbon atom alkenyl group,

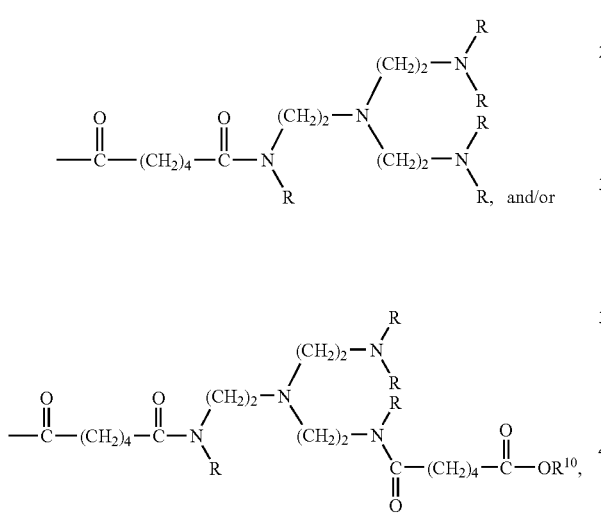

wherein $R^{10}$ is a 1-22 carbon atom alkyl group and/or a 1-22 carbon atom alkenyl group.

Aqueous fabric softeners can be prepared using the quaternized amidoamine of Example 2 with the dimethyl sulfate (Examples 5 and 6) and the quaternized amidoamine of Example 4 with the dimethyl sulfate (Examples 7 and 8). Amounts are weight percent based on the total weight of the composition. The compositions can be prepared by mixing of the ingredients.

| Material | Ex. 5 | Ex. 6 | Ex. 7 | Ex. 8 |
| --- | --- | --- | --- | --- |
| Quaternized amidoamine from Ex. 2 | 5 | 5 | — | — |
| Quaternized amidoamine from Ex. 4 | — | — | 5 | 5 |
| Glycerol monostearate | — | 1 | — | 1 |
| Perfume | 0.3 | 0.3 | 0.3 | 0.3 |
| Minors (dye, chelants, preservatives) | Q.S. | Q.S. | Q.S. | Q.S. |
| Water | Q.S. | Q.S. | Q.S. | Q.S. |

Other amidoamines can be prepared from the formulations in the table below (amounts are molar amounts):

| Diethylene triamine | Tallow acid | Adipic acid | H-Tallow Alcohol |
| --- | --- | --- | --- |
| 1 | 0.5 | 0.5 | 0 |
| 1 | 0.5 | 0.5 | 0.2 |
| 1 | 0.5 | 0.7 | |
| 1 | 1 | 0.7 | |
| 1 | 2 | 0.7 | |
| 1 | 2.5 | 0.7 | |
| 1 | 3 | 0.7 | |
| 1 | 0.5 | 1 | |
| 1 | 1 | 1 | |
| 1 | 2 | 1 | |
| 1 | 2.5 | 1 | |
| 1 | 3 | 1 | |
| 1 | 0.5 | 1.3 | |
| 1 | 1 | 1.3 | |
| 1 | 2 | 1.3 | |
| 1 | 2.5 | 1.3 | |
| 1 | 3 | 1.3 | |

What is claimed is:

1. An aqueous conditioning or softening composition comprising an oligomeric amidoamine, surfactant, and water, wherein the oligomeric amidoamine comprises a reaction product of (A), (B), and (C) wherein:

(A) represents an alkylene polyamine having the formula:

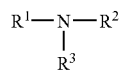

wherein $R^1$, $R^2$, $R^3$ are independently H or $-R^5-N-R^4)_2$, wherein not all of R', $R^2$, and $R^3$ are H;
$R^4$ is H or $-R^5-N-(R^8)_2$;
$R^8$ is independently H or $R^5$; and $R^5$ is (i) a $C_1$-$C_{23}$ alkylene or alkenyl group optionally substituted or branched; or (ii) an aryl group;

(B) represents a dicarboxylic acid or a reactive derivative of such acid having the formula:

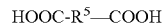

wherein $R_5$ is defined as above; and (C) represents (i) a fatty acid having the formula:

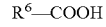

wherein $R^6$ is a linear or branched $C_6$-$C_{23}$ alkyl or alkenyl group; and/or (ii) an alkyl ester or glyceride of the fatty acid (i).

2. An oligomeric amidoamine salt formed by neutralizing the oligomeric amidoamine of claim 1 with a mineral acid and/or an organic acid.

3. An oligomeric amidoquaternary ammonium compound formed by quaternizing the oligomeric amidoamine of claim 1 with an alkylating agent.

4. The oligomeric amidoamine of claim 1, wherein the molar ratio of dicarboxylic acid (B) to polyamine (A) is about 0.5 to about 0.8.

5. The oligomeric amidoamine claim 1, wherein the molar ratio of the fatty acid (C) to the polyamine (A) is about 0.5 to about 1.5.

6. The oligomeric amidoamine of claim 1, wherein $R_5$ is a $C_1$-$C_6$ alkylene or alkenyl group optionally substituted or branched.

7. A fabric softening composition comprising an effective amount of the oligomeric amidoamine of claim 1, an oligomeric amidoamine salt of the oligomeric amdioamine, and/or an oligomeric amidoquat of the oligomeric amidoamine.

8. The fabric softening composition of claim 7 further comprising a second softening compound comprising a cationic softener and/or a nonionic softener.

9. The fabric softening composition of claim 8, wherein the second softening compound comprises a compound represented by the formula:

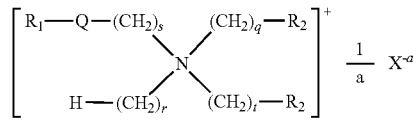

wherein Q represents a carboxyl group having the structure —OCO— and/or —COO—; $R_1$ represents an aliphatic hydrocarbon group having 8 to 22 carbon atoms; $R_2$ represents -Q-$R_1$ and/or —OH; q, r, s and t, each independently represent a number of 1 to 3; and $X^{-a}$ is an anion of valence a; and wherein the fatty ester quaternary ammonium compound is comprised of a distribution of monoester, diester and triester compounds, the monoester compound being formed when each $R_2$ is —OH; the diester compound being formed when one $R_2$ is —OH and the other $R_2$ is -Q-R1; and the triester compound being formed when each $R_2$ is -Q-R1; and wherein the normalized percentage of monoester compound in the fatty ester quaternary ammonium compound is about 31% to about 37%; the normalized percentage of diester compound is about 53% to about 59% and the normalized percentage of triester compound is about 8% to about 12%; all percentages being by weight.

10. A hair conditioning composition comprising an effective amount of the oligomeric amidoamine of claim 1, an oligomeric amidoamine salt of the oligomeric amidoamine, and/or an oligomeric amidoquat of the oligomeric amidoamine.

11. The hair conditioning composition of claim 10 further comprising a conditioning agent comprising a cationic or nonionic hair conditioner.

12. The oligomeric amidoamine of claim 1, wherein the amidoamine comprises:

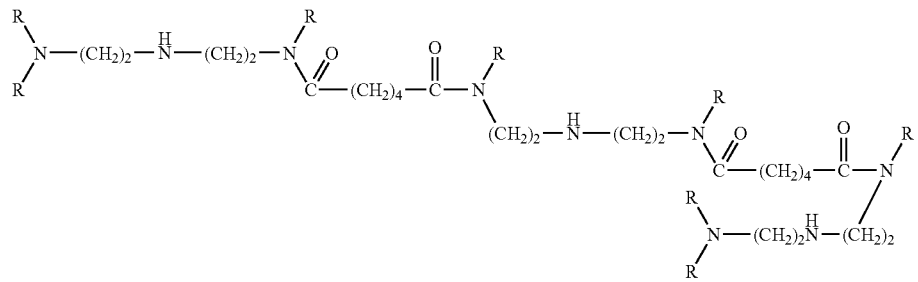

wherein R is H, a 1-22 carbon atom alkyl group, a 1-22 carbon atom alkenyl group, and/or

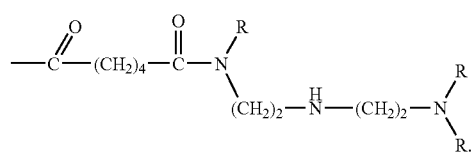

13. The oligomeric amidoamine of claim 1, wherein the amidoamine comprises

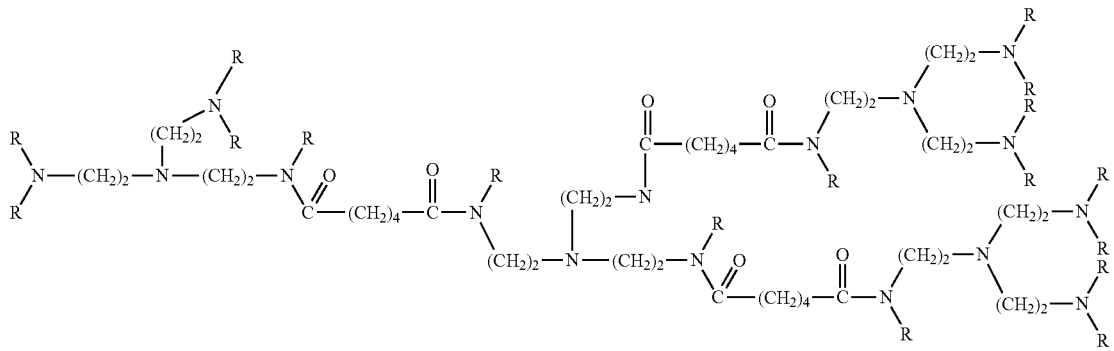

wherein R is H, a 1-22 carbon atom alkyl group, a 1-22 carbon atom alkenyl group,

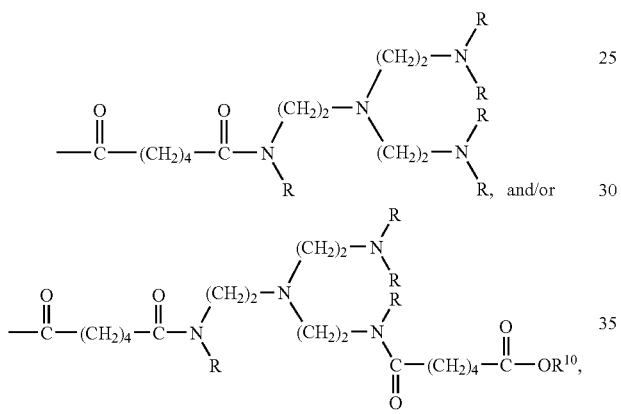

wherein $R^{10}$ is a 1-22 carbon atom alkyl group and/or a 1-22 carbon atom alkenyl group.

14. A method of softening fabrics comprising a step of contacting the fabrics to be softened with an effective amount of the fabric softening composition of claim 7.

15. A method of conditioning hair comprising a step of contacting the hair to be conditioned with an effective amount of the hair conditioning composition of claim 10.

\* \* \* \* \*